United States Patent
Curatolo et al.

(10) Patent No.: US 9,241,787 B2
(45) Date of Patent: Jan. 26, 2016

(54) INTRAOCULAR LENS WITH A PROOFED SURFACE

(71) Applicant: SIFI MedTech Srl, Lavinaio (IT)

(72) Inventors: Maria Cristina Curatolo, Aci Sant'antonio (IT); Elena Anastasi, Acireale (IT); Rosario Occhipinti Amato, Ragusa (IT)

(73) Assignee: SIFI MedTech Srl (IT)

( * ) Notice: Subject to any disclaimer, the term of this patent is extended or adjusted under 35 U.S.C. 154(b) by 106 days.

(21) Appl. No.: 13/789,057

(22) Filed: Mar. 7, 2013

(65) Prior Publication Data

US 2014/0228947 A1    Aug. 14, 2014

Related U.S. Application Data

(60) Provisional application No. 61/764,148, filed on Feb. 13, 2013.

(51) Int. Cl.
| | |
|---|---|
| *A61F 2/16* | (2006.01) |
| *B29D 11/02* | (2006.01) |
| *B29C 71/02* | (2006.01) |
| *B29C 71/04* | (2006.01) |
| *B29C 35/02* | (2006.01) |
| *B29C 59/14* | (2006.01) |
| *B29C 59/16* | (2006.01) |
| *B29C 35/08* | (2006.01) |

(52) U.S. Cl.
CPC ............... *A61F 2/16* (2013.01); *B29C 35/0266* (2013.01); *B29C 71/02* (2013.01); *B29C 71/04* (2013.01); *B29D 11/023* (2013.01); *B29C 59/14* (2013.01); *B29C 59/16* (2013.01); *B29C 2035/0827* (2013.01)

(58) Field of Classification Search
CPC ........ A61F 2/16; A61L 27/16; A61L 2430/16
USPC ....................................................... 623/6.56
See application file for complete search history.

(56) References Cited

U.S. PATENT DOCUMENTS

| | | | | |
|---|---|---|---|---|
| 4,279,795 | A * | 7/1981 | Yamashita et al. ............ | 523/112 |
| 2001/0041935 | A1 * | 11/2001 | Valyunin et al. ............. | 623/6.56 |

* cited by examiner

*Primary Examiner* — David H Willse
*Assistant Examiner* — Tiffany Shipmon
(74) *Attorney, Agent, or Firm* — Levine Bagade Han LLP

(57) ABSTRACT

Methods and apparatus for an intraocular lens with a proofed surface are disclosed. The proofed surface functions as a barrier to fluid diffusion inside the material and within vacuoles. By preventing the interstitial filling of fluid, the formation of spots inside the polymer matrix is inhibited or reduced. The proofed surface of the intraocular lenses is a highly stable re-assembled surface without any coating or grafting.

10 Claims, 1 Drawing Sheet

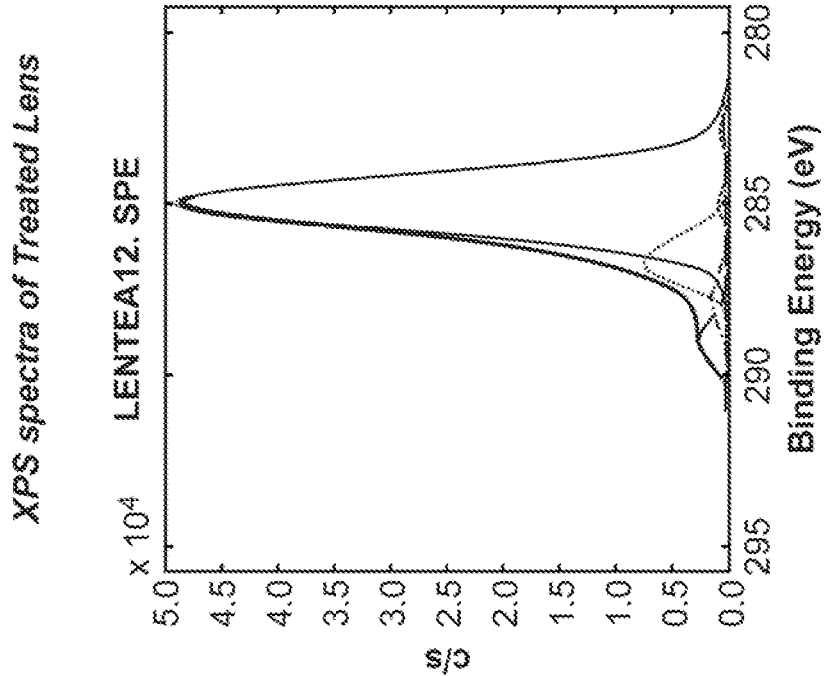
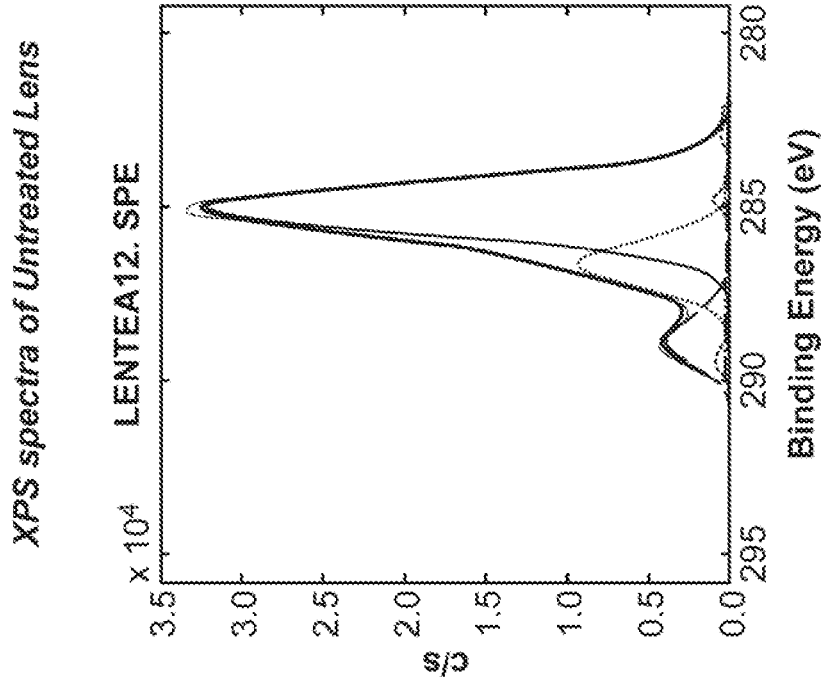

INTRAOCULAR LENS WITH A PROOFED SURFACE

CROSS-REFERENCE TO RELATED APPLICATIONS

This application claims the benefit of priority to U.S. Prov. App. 61/764,148 filed Feb. 13, 2013, which is incorporated herein by reference in its entirety.

FIELD OF THE INVENTION

The present invention relates to ophthalmic prostheses, such as intraocular lenses, having a proofed surface. These intraocular lenses exhibit reduced or eliminated loss of transparency and homogeneity, typically due to water sorption and diffusion in the polymer after implantation into the eye and most often a cause of serious visual disturbances for patients.

BACKGROUND OF THE INVENTION

Transport of fluids through polymeric materials is an important factor in several biomedical applications. Controlling of transport mechanisms in polymeric materials is highly important in order to achieve significant improvement in such areas as that of ophthalmic prosthesis.

A concerning unresolved problem, especially with the hydrophobic ac intraocular lenses, is that lenses tend to present formations of reflective spots in their polymeric structure when implanted into a patient's eye. Water particles are able to enter into vacuoles of the polymeric matrix thereby changing the refractive index of the lens at those points. The actual cause of this phenomenon remains unresolved. The effects at the clinical level are discussed and varies from loss of visual acuity and glare to other visual disturbances, Substitution of the lens in some cases may be required.

Many prior attempts at improving intraocular lens materials are included altering the chemical structure and composition of the lens material to avoid the formation of reflective and refractive spots; however, the bulk properties of the lens materials are affected. Changing the chemical properties to reduce the number and dimension of vacuoles or increasing the water content to control the concentration gradient compromises the mechanical and optical properties and also changes the biocompatibility.

Thus, there is a need for an acrylic foldable intraocular lens that has a substantially reduced or eliminated tendency to form these regions in its structure by maintaining unvaried bulk properties.

SUMMARY OF THE INVENTION

The present invention provides such a lens with a proofed surface functioning as barrier to the fluid diffusion inside the material and within the vacuoles. By preventing the interstitial filling of fluid, the formation of spots inside the polymer matrix is inhibited or reduced. The proofed surface of intraocular tenses is a highly stable re-assembled surface without any coating or grafting.

BRIEF DESCRIPTION OF THE DRAWINGS

FIG. 1 shows an example of an X-ray photoelectron spectroscopy spectra following a hydrogen peroxide gas plasma treatment.

DETAILED DESCRIPTION OF THE INVENTION

In accordance with aspects of the present invention, it relates to an intraocular lens (IOL) having a proofed surface which controls fluid sorption and diffusion inside the polymer matrix as well as reflective-refractive spots formation.

An IOL with a proofed surface can be used to support a surgeon in optimizing post-operative outcomes for refractive and cataract surgery. An implanted IOL with a proofed surface is not affected by a decrease of optical performance and does not complicate a post surgical course of patients implanted with standard IOLs (e.g., monofocal IOLs) and/or advanced optics (e.g., multifocal IOLs, toric IOLs or a combination thereof).

The described IOL with a proofed surface has unchanged bulk properties and water content. The described IOL with a proofed surface also controls water spot formation inside the polymer matrix by preventing water access and maintains the same interstitial configuration of the bulk material and unchanged water content.

The described IOL with a proofed surface can be made of a new or an conventional material. For instance, IOLs with a proofed surface which are made of conventional hydrophobic materials having large and numerous vacuoles within, can prevent the formation of water spots. These described IOLs can also have an improved clinical performance without any decrease of transparency and homogeneity. Since the described IOLs have a proofed surface but unchanged bulk properties, the existing clinical history about biocompatibility optical and mechanical outcomes does not need to be reconstructed.

The proofed surface of IOLs is a highly stable self-reassembled surface without a coating or grafting which can be proofed at every step of the production process.

The IOLs with a proofed surface may also have reduced free species with low molecular weight, for low molecular weight species may result from residual monomers or additives.

The IOLs with a proofed surface may further have some clinical benefits in patients implanted with premium IOLs, with advanced optics, through micro-incision surgery, Optical outcomes of surface proofed IOLs may be improved and since the porosity in the bulk material is unchanged and the mechanical properties of unfolding and deformability are maintained, the low invasiveness of surgery and stability of IOLs are also preserved.

The IOLs with a proofed surface may further generate some industrial benefits since it may be unnecessary to develop new IOL materials for preventing postsurgical formation of reflective spots. Proofing the surface of an existing IOL may improve the clinical optical outcomes and may also continue to allow the use pre-existing clinical data, In one embodiment of the present invention, the intraocular lens with a proofed surface has a reduced chain segment motion at the water/polymer interface.

In another embodiment of the present invention, the intraocular lens with a proofed surface has a gradient of porosity from surface to bulk, porosity of an intraocular lens with a proofed surface is highly reduced at the water/polymer interface than in bulk.

In another embodiment of this invention, density of linkages between molecular chains is selectively enhanced at the superficial stratus of the surface proofed lens material.

The surface proofed lens material has been treated at the superficial stratus through a treatment of curing selectively applied to the surface.

In another embodiment of this invention the surface curing treatments, selectively applied to the surface in order to obtain a proofed surface, are based on an oxidative mechanism.

In another embodiment of this invention the oxidative mechanism, on which the surface curing treatments are based, uses plasma.

In another embodiment of this invention, hydrogen peroxide is used as gas plasma.

In another embodiment of this invention, the oxidative mechanism, on which the surface curing treatments are based, uses UV.

In another embodiment, the UV surface curing treatments are performed when the intraocular tens has been implanted into the patient's eye. A UV activated curing agent, able to migrate and concentrate on the lens surface, is used.

In another embodiment of this invention, the surface curing treatments are based on thermal mechanisms. The thermal mechanism, on which the surface curing treatments are based, uses a selective surface heating of the intraocular lens. The selective surface heating is obtained by tuning two parameter as time and temperature. A thermal activated curing agent, able to migrate and concentrate on lens surface, is used.

In an aspect of this invention, the intraocular lens is a foldable intraocular tens.

In an aspect of this invention, the intraocular lens is an intraocular lens with a monofocal, multifocal toric or multifocal/toric optic.

In an aspect of this invention, the intraocular lens is an intraocular lens for micro-incision surgery.

In another aspect of this invention, the intraocular lens is preloaded in a deployment instrument.

The intraocular lens polymer is a copolymer. The intraocular tens polymer is an acrylic polymer or a silicon polymer.

Various aspects of the present invention are further described by way of the following example, The example is offered by way of illustration and is not intended to be limiting in any way.

EXAMPLE 1

The following example refers to X-ray photoelectron spectroscopy (XPS) surface analysis of intraocular tenses subjected to the hydrogen peroxide gas plasma treatment, A surface proofing is shown due to the increase of apolar groups. As shown in the XPS spectra, an increase of C—C bonds and a decrease of C(=O)O and C—O—C bonds occurs after the hydrogen peroxide gas plasma treatment as indicated in the graphs of FIG. 1 and Table 1 below. The graph to the left shows the XPS spectra of an untreated lens in comparison to the graph to the right which shows the XPS spectra of a treated lens.

Radicals present in the plasma phase generate a reaction allowing a transfer of an hydrogen from the polymeric chains to the OH*radicals. This generates alkyl radicals, in the polymeric chain (R*).

The presence of two or more alkyl radicals R*, in accordance with XPS spectra FIG. 1 and Table 1 below, produces the formation of C—C bonds and therefore an increase of cross linking in the surface polymeric network.

The radicals R* rearrange and stabilize through the loss of a chain segment (*O—R). Therefore this rearrangement produces, in accordance with XPS spectra FIG. 1 and Table 1 below, a decrease of C(=O)O and C—O—C bonds in polymeric chains on surface.

TABLE 1

| Reference spectrum from an untreated and treated lens. | | | | | | | | |
|---|---|---|---|---|---|---|---|---|
| Band | Pos | Delta | B_FWHM | G_FWHM | Height | Area | % Gauss | % Area |
| Reference spectrum from UNTREATED LENS (XPS SPECTRUM) Region: Cls | | | | | | | | |
| 1 | 285.01 | 0.00 | 1.69 | 1.69 | 31945 | 58906 | 94 | 73.10 C—C C—H |
| 2 | 286.60 | 1.59 | 1.58 | 1.58 | 9162 | 15415 | 100 | 19.13 C—O—C |
| 3 | 287.80 | 2.79 | 1.50 | 1.50 | 10 | 16 | 100 | 0.02 |
| 4 | 288.82 | 3.81 | 1.50 | 1.50 | 3908 | 6241 | 100 | 7.74 C(=O)O |
| Reference spectrum from TREATED LENS (XPS SPECTRUM) Region: Cls | | | | | | | | |
| 1 | 284.98 | 0.00 | 1.81 | 1.81 | 47907 | 94264 | 95 | 84.00 C—C C—H |
| 2 | 286.60 | 1.62 | 1.50 | 1.50 | 7494 | 11966 | 100 | 10.66 C—O—C |
| 3 | 287.80 | 2.82 | 1.50 | 1.50 | 1464 | 2337 | 100 | 2.08 |
| 4 | 288.95 | 3.96 | 1.50 | 1.50 | 2284 | 3646 | 100 | 3.25 C(=O)O |

The applications of the devices and methods discussed above are not limited to the treatment of lenses but may include any number of further applications. Modification of the above-described assemblies and methods for carrying out the invention, combinations between different variations as practicable, and variations of aspects of the invention that are obvious to those of skill in the art are intended to be within the scope of the claims.

What is claimed is:

1. An intraocular lens, comprising:
    a lens having a proofed surface which omits a coating or grafting,
    wherein the proofed surface is formed via selective self-reassembly when exposed to an oxidative mechanism such that bulk properties and a water content of the lens remains unchanged,
    wherein a transparency and homogeneity of the lens is improved relative to a lens having an un-proofed surface, and
    wherein reflective spot formation within the lens is also reduced or inhibited relative to the lens having an un-proofed surface.

2. The intraocular lens of claim 1 wherein a chain segment motion at a fluidlpolymer interface is reduced.

3. The intraocular lens of the claim 1 wherein a porosity at a fluid/polymer interface is reduced relative to a porosity of the lens having the un-proofed surface and wherein a gradient of porosity exists from surface to bulk of the lens having the proofed surface.

4. The intraocular lens of the claim 1 wherein a density of linkages of one or more molecular chains at a superficial stratus of a surface of the lens is increased.

5. The intraocular lens of the claim 1 wherein the lens comprises hydrophobic and hydrophilic copolymers.

6. The intraocular lens of the claim 1 wherein the lens comprises a monofocal optic.

7. The intraocular lens of the claim 1 wherein the lens comprises a multifocal optic.

8. The intraocular lens of the claim 1 wherein the lens comprises a toric optic.

9. The intraocular lens of the claim 1 wherein the lens comprises a multifocal and toric optic.

10. The intraocular lens of claim 1 wherein the lens is preloaded in a deployment instrument.

\* \* \* \* \*